(12) United States Patent
McBride et al.

(10) Patent No.: US 9,066,761 B2
(45) Date of Patent: Jun. 30, 2015

(54) SPINAL IMPLANT SYSTEM AND METHOD

(75) Inventors: Larry McBride, Memphis, TN (US); David Fiorella, Arlington, VA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 281 days.

(21) Appl. No.: 13/588,718

(22) Filed: Aug. 17, 2012

(65) Prior Publication Data
US 2014/0052187 A1 Feb. 20, 2014

(51) Int. Cl.
*A61B 17/70* (2006.01)

(52) U.S. Cl.
CPC ............ *A61B 17/7085* (2013.01); *A61B 17/708* (2013.01)

(58) Field of Classification Search
CPC ........... A61B 17/7074; A61B 17/7076; A61B 17/7077; A61B 17/7079; A61B 17/708; A61B 17/7083; A61B 17/7085; A61B 17/7086; A61B 17/7088; A61B 17/7089; A61B 17/7091; A61B 17/7082
USPC ......... 606/246–279, 104, 86 A, 86 B, 99, 305
See application file for complete search history.

(56) References Cited

U.S. PATENT DOCUMENTS

| | | | | |
|---|---|---|---|---|
| 7,462,182 B2 * | 12/2008 | Lim | | 606/99 |
| 7,575,581 B2 * | 8/2009 | Lovell | | 606/104 |
| 7,597,694 B2 * | 10/2009 | Lim et al. | | 606/86 A |
| 7,758,584 B2 * | 7/2010 | Bankoski et al. | | 606/104 |
| 7,931,673 B2 * | 4/2011 | Hestad et al. | | 606/246 |
| 7,947,046 B2 * | 5/2011 | Justis et al. | | 606/86 A |
| 7,951,175 B2 * | 5/2011 | Chao et al. | | 606/279 |
| 8,235,997 B2 * | 8/2012 | Hoffman et al. | | 606/86 A |
| 8,323,286 B2 * | 12/2012 | Justis | | 606/86 A |
| 8,439,922 B1 * | 5/2013 | Arnold et al. | | 606/86 A |
| 8,439,924 B1 * | 5/2013 | McBride et al. | | 606/86 A |
| 8,460,300 B2 * | 6/2013 | Hestad et al. | | 606/86 A |
| 8,545,505 B2 * | 10/2013 | Sandstrom et al. | | 606/86 A |
| 8,617,218 B2 * | 12/2013 | Justis et al. | | 606/278 |
| 8,709,044 B2 * | 4/2014 | Chao et al. | | 606/246 |
| 2008/0015601 A1 * | 1/2008 | Castro et al. | | 606/86 |
| 2008/0228233 A1 * | 9/2008 | Hoffman et al. | | 606/86 A |
| 2009/0157125 A1 * | 6/2009 | Hoffman et al. | | 606/86 A |
| 2009/0228054 A1 * | 9/2009 | Hoffman et al. | | 606/86 A |
| 2009/0228055 A1 * | 9/2009 | Jackson | | 606/86 A |
| 2011/0022093 A1 * | 1/2011 | Sherman et al. | | 606/254 |
| 2011/0040335 A1 * | 2/2011 | Stihl et al. | | 606/302 |
| 2011/0087298 A1 * | 4/2011 | Jones | | 606/86 A |
| 2011/0218581 A1 * | 9/2011 | Justis | | 606/86 A |
| 2013/0018419 A1 * | 1/2013 | Rezach et al. | | 606/264 |
| 2013/0041415 A1 * | 2/2013 | Justis | | 606/86 A |
| 2013/0261679 A1 * | 10/2013 | McBride et al. | | 606/86 A |
| 2014/0148865 A1 * | 5/2014 | Hennard et al. | | 606/86 A |

* cited by examiner

*Primary Examiner* — Eduardo C Robert
*Assistant Examiner* — Lynnsy Summitt
(74) *Attorney, Agent, or Firm* — Sorell Lenna & Schmidt LLP

(57) ABSTRACT

An extender comprises a first extension including a first wall and extending between a proximal end and a distal end. The first wall defines an axial cavity including a distal portion, at least one ramp and a proximal portion. A second extension includes a projection. The projection is disposable in a first position with the distal portion of the axial cavity and the distal end of the first extension is disposed in a non-expanded orientation. The projection is slidably engageable with the at least one ramp for movement to a second position such that the projection is disposed with the proximal portion of the axial cavity and the distal end of the first extension is disposed in an expanded orientation. Methods of use are disclosed.

20 Claims, 10 Drawing Sheets

SPINAL IMPLANT SYSTEM AND METHOD

TECHNICAL FIELD

The present disclosure generally relates to medical devices for the treatment of musculoskeletal disorders, and more particularly to a surgical system for implant delivery to a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior art technologies.

SUMMARY

In one embodiment, in accordance with the principles of the present disclosure, an extender is provided. The extender comprises a first extension including a first wall and extending between a proximal end and a distal end. The first wall defines an axial cavity including a distal portion having a first dimension, an intermediate portion having at least one ramp and a proximal portion having a second dimension. The first dimension is greater than the second dimension. The distal end includes at least one fixation surface. A second extension extends from adjacent the proximal end of the first extension to a distal end of the second extension. The distal end includes a projection. The first extension is configured for axial translation relative to the second extension such that the projection is disposable in the axial cavity in a first position such that the projection is disposed with the distal portion of the axial cavity and the distal end of the first extension is disposed in a non-expanded orientation. The projection is slidably engageable with the at least one ramp for movement to a second position such that the projection is disposed with the proximal portion of the axial cavity and the distal end of the first extension is disposed in an expanded orientation.

In one embodiment, the extender comprises a first member defining a first longitudinal axis and extending between a proximal end and a distal end. The first member includes two spaced apart first extensions. Each of the first extensions includes a wall including a first sliding contact surface that defines an axial slot including a distal portion having a first dimension, an intermediate portion having at least one ramp and a proximal portion having a second dimension. The first dimension is greater than the second dimension. Each of the first extensions include an expandable capture member having at least one fixation surface adjacent the distal end. A second member extends from adjacent the proximal end of the first member to a distal end of the second member. The second member includes two spaced apart second extensions. Each of the second extensions includes a projection having a second sliding contact surface. The first member is configured for axial translation in a first direction relative to the second member such that the projections are disposable in respective axial slots in a first position such that each of the projections are disposed with the distal portion of the respective axial slot and the respective capture member is disposed in a non-expanded orientation. The first sliding contact surfaces are engageable with the second sliding contact surfaces for movement to a second position such that the projections are disposed with the proximal portion of the axial slot and a respective capture member is disposed in an expanded orientation.

In one embodiment, in accordance with the principles of the present disclosure, a spinal implant system is provided. The spinal implant system comprises an extender comprising a first member defining a first longitudinal axis and extending between a proximal end and a distal end. The first member includes a pair of spaced apart first extensions. Each of the first extensions include a wall including a first sliding contact surface that defines an axial slot including a distal portion having a first dimension, an intermediate portion having a first ramp and a second ramp and a proximal portion having a second dimension. The first dimension is greater than the second dimension. The ramps are tapered to the second dimension. The wall of each of the first extensions includes a first flange. Each of the first extensions include an expandable capture member having at least one fixation surface adjacent the distal end. A second member extends from adjacent to the proximal end of the first member to a distal end of the second member. The second member includes a pair of spaced apart second extensions. Each of the second extensions includes a projection including a second sliding contact surface. The distal end of each of the second extensions include a second flange that defines a flange cavity configured for disposal of the first flange such that the second flange slidably engages the first flange. An actuator is fixed with the second member and engageable with the first member to cause axial translation of the first member relative to the second member. A bone fastener includes a proximal portion that defines an implant cavity and a distal portion configured to penetrate tissue. The actuator is engageable to cause the axial translation of the first member in a first direction relative to the second member such that the projections are disposable in respective axial slots in a first position such that each of the projections are disposed with the distal portion of a respective axial slot and the respective capture member is disposed in a non-expanded orientation such that the at least one fixation surface captures the bone fastener. The first sliding contact surfaces are engageable with the second sliding contact surfaces for movement to a second position such that the projections are disposed with the proximal portion of the axial slot and the respective capture member is disposed in an expanded orientation to release the bone fastener.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
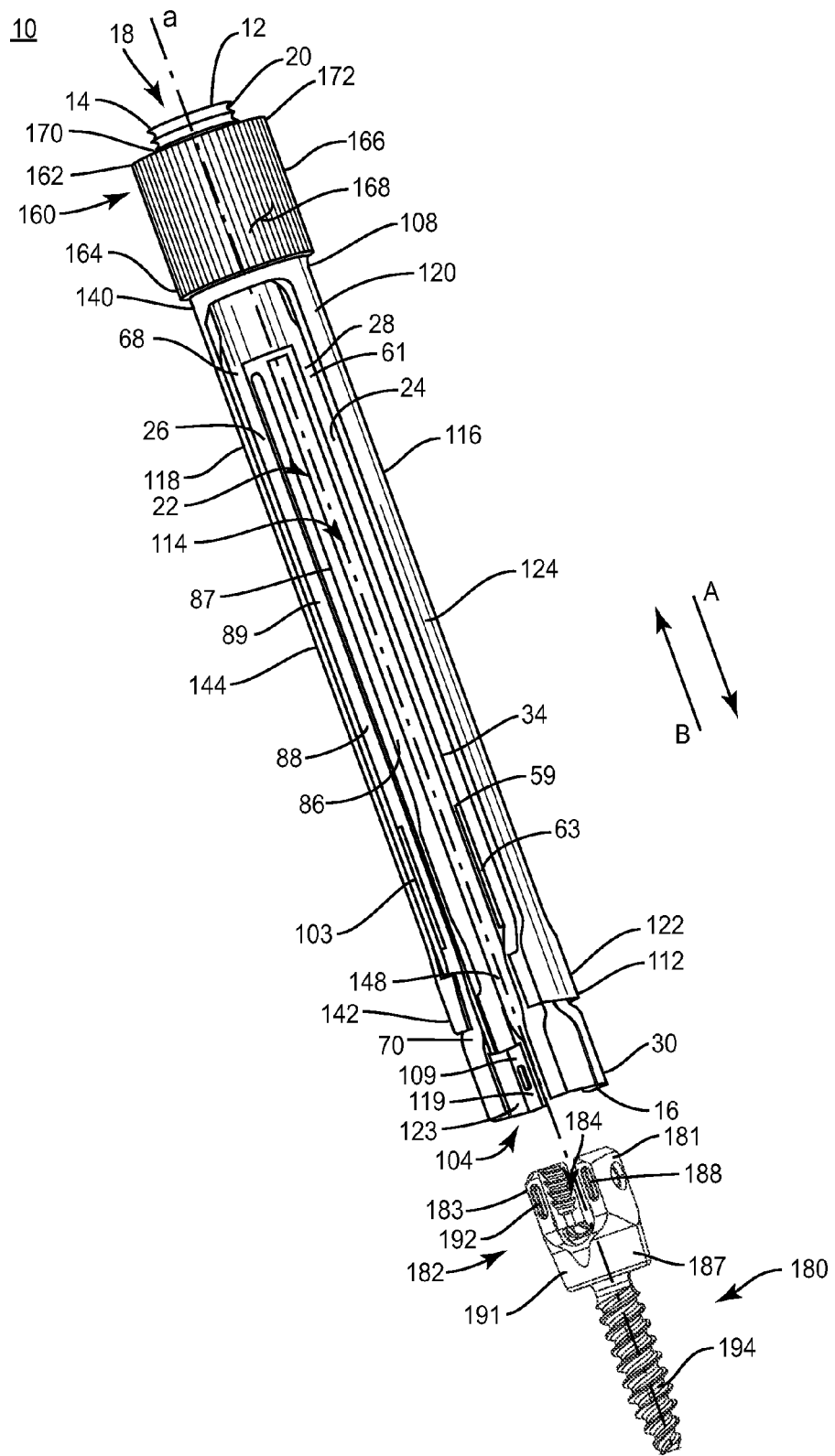
FIG. 1 is a perspective view of one particular embodiment of a system in accordance with the principles of the present disclosure.
Figure 2:
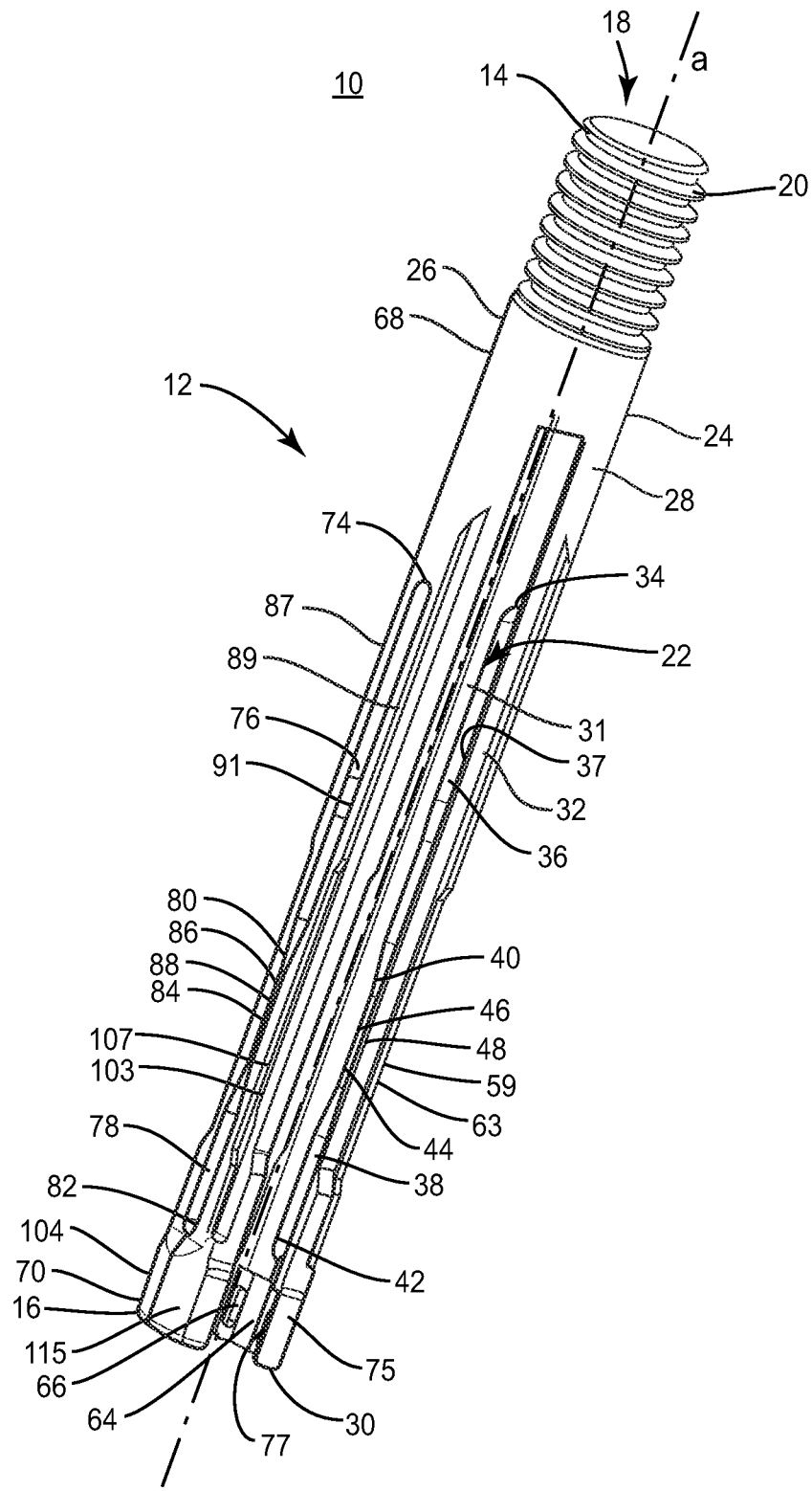
FIG. 2 is a perspective view of components of the system shown in FIG. 1.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine. It is envisioned that the surgical implant system can include a bone fastener having a head with a cut that allows the head to be captured and retained under tension and lateral compression. It is further envisioned that the tension may be applied through a member, such as, for example, an extender and that compression may be applied through another member, such as, for example, a sleeve.

It is envisioned that the system may include instruments that are connected or attached to an extender(s) such as, for example, a lateral translation handle or derotaton instruments. It is further envisioned that the system may have an extender with a quick release mechanism to allow the extender to slide into engagement with an implant. It is contemplated that the system can include an extender having features that prevent an implant from rotating. In one embodiment, one or all of the components of the surgical system are disposable, peel-pack, pre-packed sterile devices used with an implant. One or all of the components of the surgical system may be reusable. The surgical system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, postero- rior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-9, there is illustrated components of a surgical system, such as, for example, a spinal implant system 10 in accordance with the principles of the present disclosure.

The components of spinal implant system 10 can be fabricated from biologically acceptable materials suitable for medical applications, including metals, synthetic polymers, ceramics and bone material and/or their composites, depending on the particular application and/or preference of a medical practitioner. For example, the components of spinal implant system 10, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elastoplastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a minimally invasive procedure, including percutaneous techniques, mini-open and open surgical techniques to deliver and introduce an implant, such as, for example, a bone fastener, at a surgical site within a body of a patient, for example, a section of a spine. It is contemplated that the spinal implant system and method may be employed with treatments using minimally invasive and percutaneous techniques.

Spinal implant system 10 includes a first member, such as, for example, an inner sleeve 12. Inner sleeve 12 extends between a proximal end 14 and a distal end 16. Inner sleeve 12 defines a first longitudinal axis a, that extends between ends 14, 16. Proximal end 14 includes an inner surface 18 and an outer threaded surface 20. Outer threaded surface 20 is configured for fixation with an actuator, as described herein.

Inner sleeve 12 has a cylindrical cross-section configuration. It is contemplated that the cross-section of inner sleeve 12 may have various configurations, for example, round, oval, rectangular, polygonal, irregular, tapered, offset, staggered, uniform and non-uniform. It is further envisioned that one or all of the surfaces of inner sleeve 12 may have alternate surface configurations, such as, for example, rough, threaded for connection with surgical instruments, arcuate, undulating, porous, semi-porous, dimpled, polished and/or textured according to the requirements of a particular application.

Inner sleeve 12 includes an implant cavity, such as, for example, channel 22 that extends through sleeve 12. Channel 22 has a circular cross-section configuration. It is contemplated that the cross-section of channel 22 may have various configurations, for example, round, oval, rectangular, polygonal, irregular, tapered, offset, staggered, uniform and non-uniform. Channel 22 is configured for disposal of a vertebral construct, such as a vertebral rod.

Inner sleeve 12 includes two spaced apart first extensions 24, 26. Extension 24 extends between a proximal end 28 and a distal end 30. Extension 24 includes a wall 34. Wall 34 has a uniform thickness along its length. It is envisioned that wall 34 may have a non-uniform thickness, tapered configuration, arcuate, staggered and/or offset portions. Wall 34 includes cantilevered arms 31, 32 extending from proximal end 28. Arms 31, 32 are resiliently biased inwardly towards each other and/or in a convergent configuration to a non-expanded orientation of inner sleeve 12.

Wall 34 has a first sliding contact surface, which includes a surface 36 and a surface 37. Surfaces 36, 37 have a smooth and even configuration for movable engagement with a surface of an outer sleeve, discussed below. It is envisioned that surfaces 36, 37 may have various surface configurations, such as those alternatives described herein.

Figure 4:
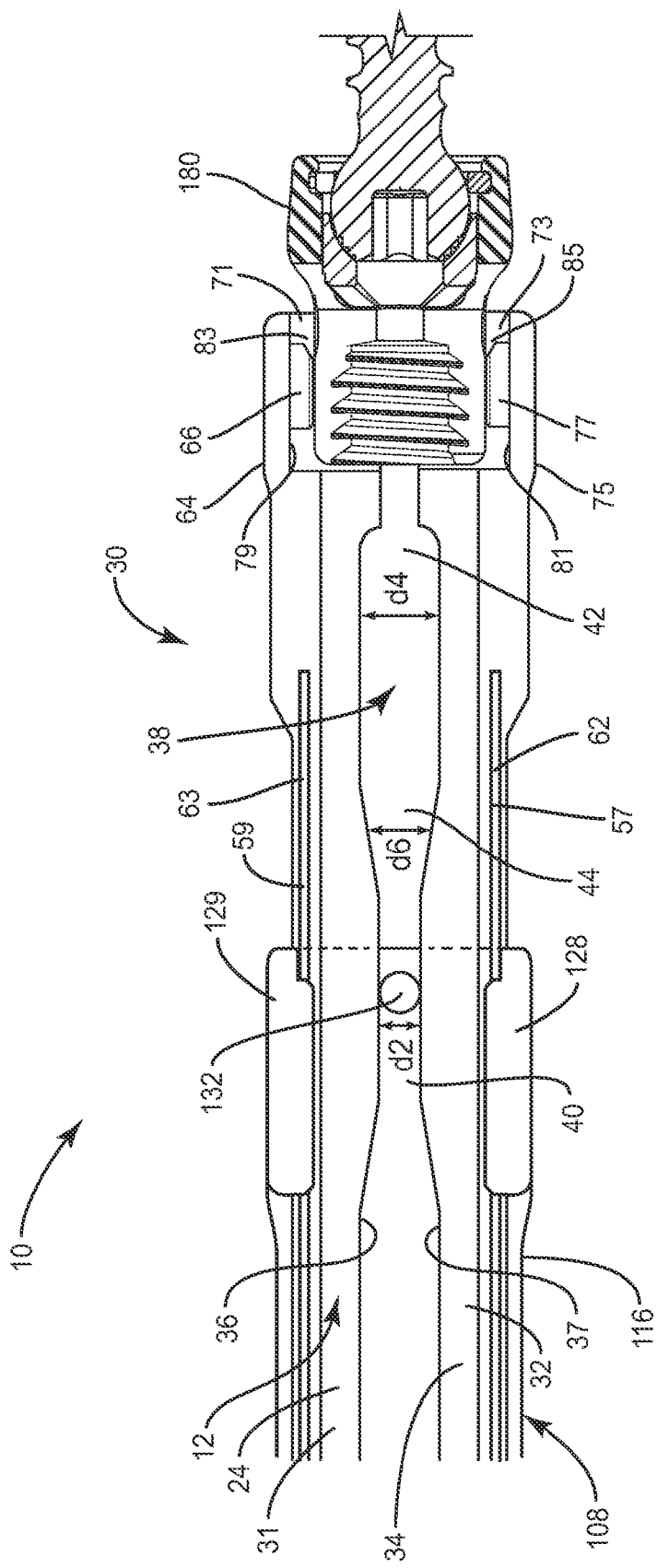
FIG. 4 is a break away cross section view of the system shown in FIG. 1.
Figure 7:
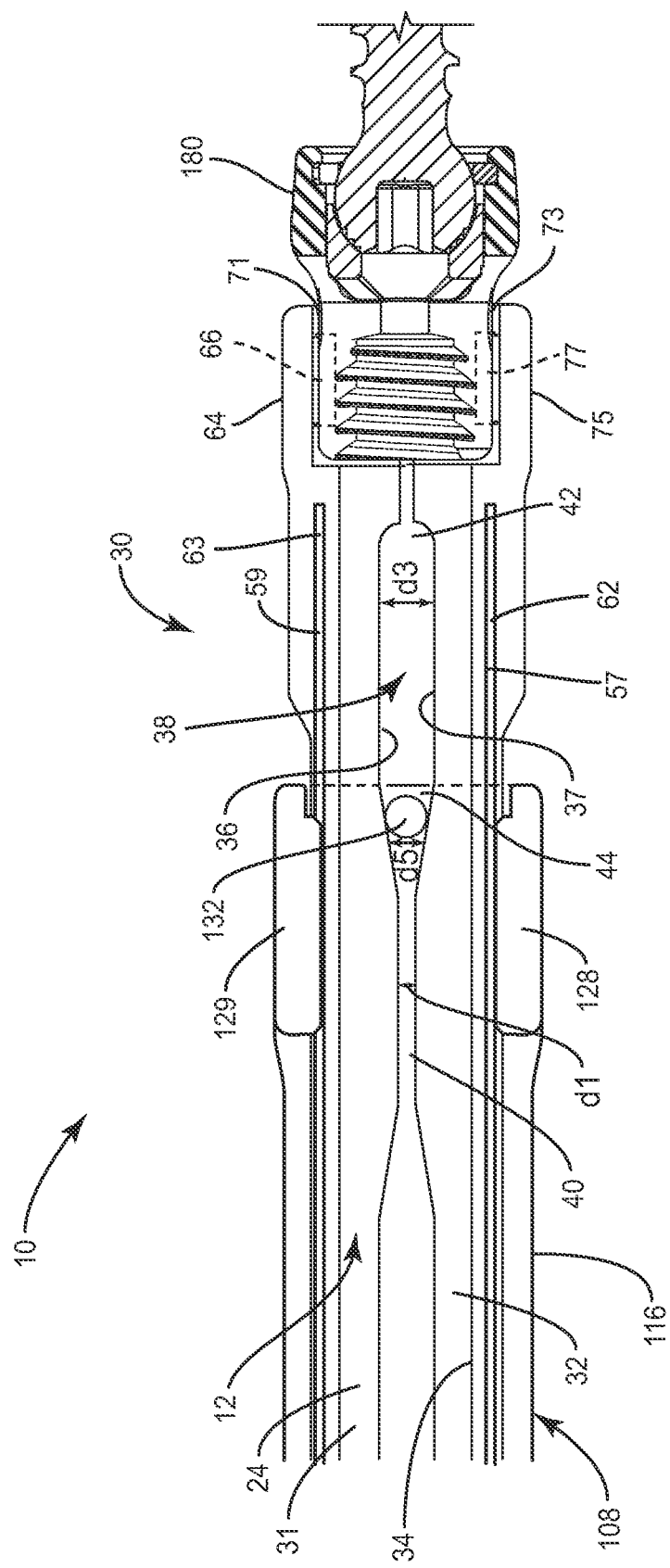
FIG. 7 is a break away cross section view of the system shown in FIG. 1.
Figure 8:
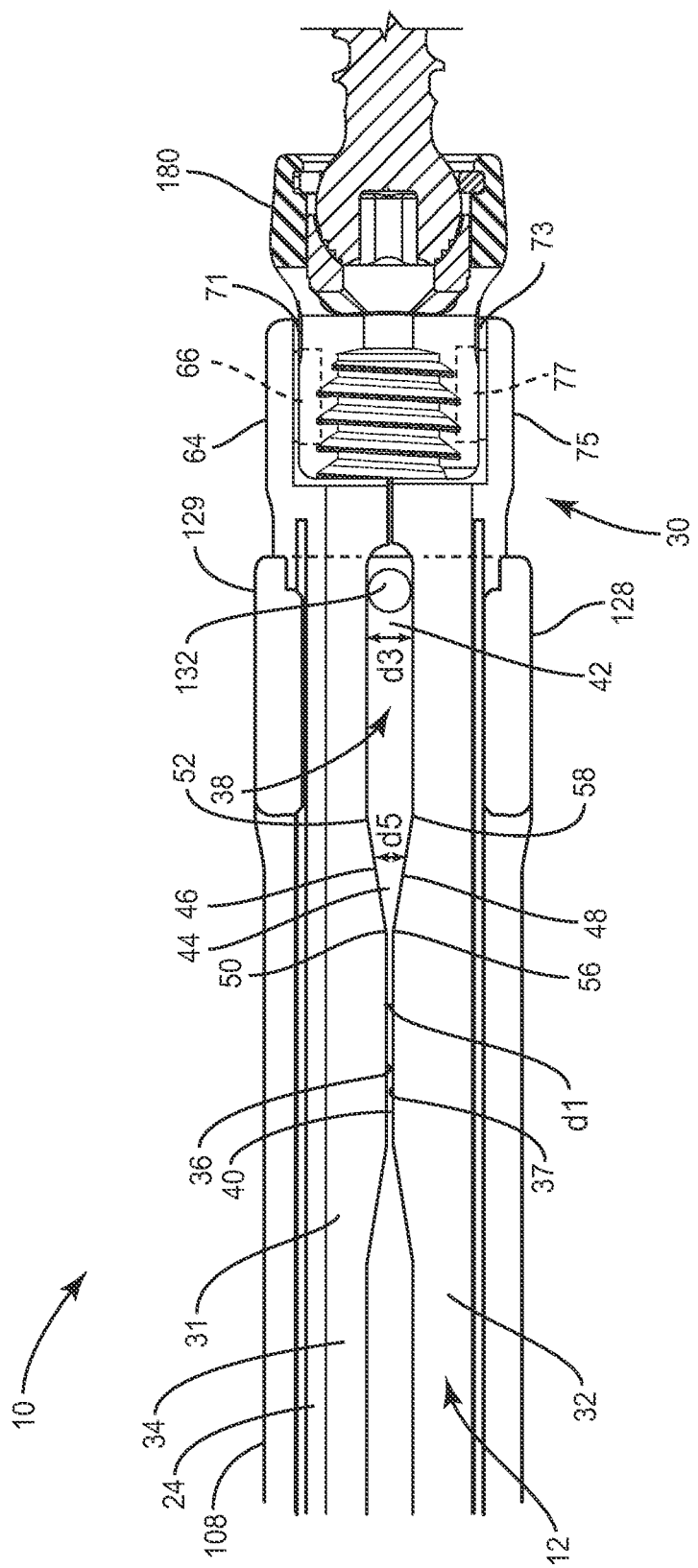
FIG. 8 is a break away cross section view of the system shown in FIG. 1.

Surfaces 36, 37 are spaced apart to define an axial cavity, such as, for example, an axial slot 38 disposed adjacent distal end 30, as shown in FIGS. 4, 7 and 8. Axial slot 38 extends between a proximal portion 40 and a distal portion 42. Surfaces 36, 37 are spaced apart a distance d1 (FIGS. 7 and 8) adjacent proximal portion 40 in the non-expanded orientation of inner sleeve 12. Inner sleeve 12 is expandable to an expanded orientation such that surfaces 36, 37 are spaced apart a distance d2 (FIG. 4) adjacent proximal portion 40. As such, axial slot 38 can be expanded and contracted adjacent proximal portion 40 within a range of expansion between distance d1 and distance d2. In one embodiment, dimension d2 is greater than dimension d1.

Surfaces 36, 37 are spaced apart a distance d3 (FIGS. 7 and 8) adjacent distal portion 42 in the non-expanded orientation of inner sleeve 12. Inner sleeve 12 is expandable to an expanded orientation such that surfaces 36, 37 are spaced apart a distance d4 (FIG. 4) adjacent distal portion 42. As such, axial slot 38 can be expanded and contracted adjacent distal portion 42 within a range of expansion between distance d3 and distance d4. In one embodiment, dimension d4 is greater than dimension d3.

An intermediate portion 44 of slot 38 is disposed between portions 40, 42. Surface 36 defines a first ramp 46 adjacent intermediate portion 44. Ramp 46 extends between a proximal end 50 and a distal end 52, which define an inclination therebetween that facilitates expansion of inner sleeve 12 between the non-expanded orientation and the expanded orientation. Surface 37 defines a second ramp 48 adjacent intermediate portion 44. Ramp 48 extends between a proximal end 56 and a distal end 58, which define an inclination therebetween that facilitates expansion of inner sleeve 12 between the non-expanded orientation and the expanded orientation.

Ramps 46, 48 are spaced apart an average distance d5 (FIGS. 7 and 8) adjacent intermediate portion 44 in the non-expanded orientation of inner sleeve 12. Inner sleeve 12 is expandable to the expanded orientation such that ramps 46, 48 are spaced apart an average distance d6 (FIG. 4) adjacent intermediate portion 44. As such, axial slot 38 can be expanded and contracted adjacent intermediate portion 44 within a range of expansion between distance d5 and distance d6. In one embodiment, dimension d6 is greater than dimension d5.

Wall 34 includes first flanges 62, 63. Flanges 62, 63 are disposed on opposing sides of wall 34. Flange 62 includes a ledge 57 that extends from a proximal end to a distal end. Flange 63 includes a ledge 59 that extends from a proximal end to a distal end. Flanges 62, 63 are configured for engagement with the distal end of an outer sleeve for slidable engagement, as described herein.

Cantilevered arm 31 includes a capture member 64 disposed adjacent a distal end thereof. Capture member 64 includes an inner surface 71 that defines an implant cavity configured for disposal of at least a portion of an implant, such as, for example, a bone fastener. Inner surface 71 includes at least one fixation surface, such as, for example, a projection 66 that extends into the implant cavity of capture member 64 to engage the bone fastener for retaining the bone fastener with inner sleeve 12. Inner surface 71 includes a planar face 79 and an arcuate face 83. It is contemplated that all or only a portion of inner surface 71 may have alternate surface configurations to enhance fixation with the bone fastener, such as, for example, dimpled and/or textured. It is contemplated that the projection may include a nail configuration, raised elements and/or spikes to facilitate engagement of the capture member with the bone fastener.

Cantilevered arm 32 includes a capture member 75 disposed adjacent a distal end thereof. Capture member 75 includes an inner surface 73 that defines an implant cavity configured for disposal of at least a portion of an implant, such as, for example, a bone fastener. Inner surface 73 includes at least one fixation surface, such as, for example, a projection 77 that extends into the implant cavity of capture member 75 to engage the bone fastener for retaining the bone fastener with inner sleeve 12. Inner surface 73 includes a planar face 81 and an arcuate face 85. It is contemplated that all or only a portion of inner surface 73 may have alternate surface configurations, similar to those described herein.

Capture member 64 extends from arm 31 and capture member 75 extends from arm 32 such that members 64, 75 are biased for engagement due to the bias of arms 31, 32. Members 64, 75 are movable between a non-expanded orientation (FIGS. 7 and 8) and an expanded orientation (FIG. 4). In the non-expanded orientation, the surfaces of members 64, 75 are disposed in a flush contacting engagement such that, for example, members 64, 75 capture and/or retain the bone fastener. Projections 66, 77 engage the bone fastener to releasably lock the bone fastener with members 64, 75. Members 64, 75 are expandable and separable, via engagement with the outer sleeve as described herein, to dispose members 64, 75 in the expanded orientation. In the expanded orientation, members 64, 75 are spaced apart such that, for example, members 64, 75 release and/or eject the bone fastener from members 64, 75. Projections 66, 77 disengage from the bone fastener.

Extension 26 extends between a proximal end 68 and a distal end 70. Extension 26 includes a wall 74. Wall 74 has a uniform thickness along its length. It is envisioned that wall 74 may have a non-uniform thickness, tapered configuration, arcuate, staggered and/or offset portions. Wall 74 includes cantilevered arms 87, 89 extending from proximal end 68. Arms 87, 89 are resiliently biased inwardly towards each other and/or in a convergent configuration to a non-expanded orientation of inner sleeve 12.

Figure 3:
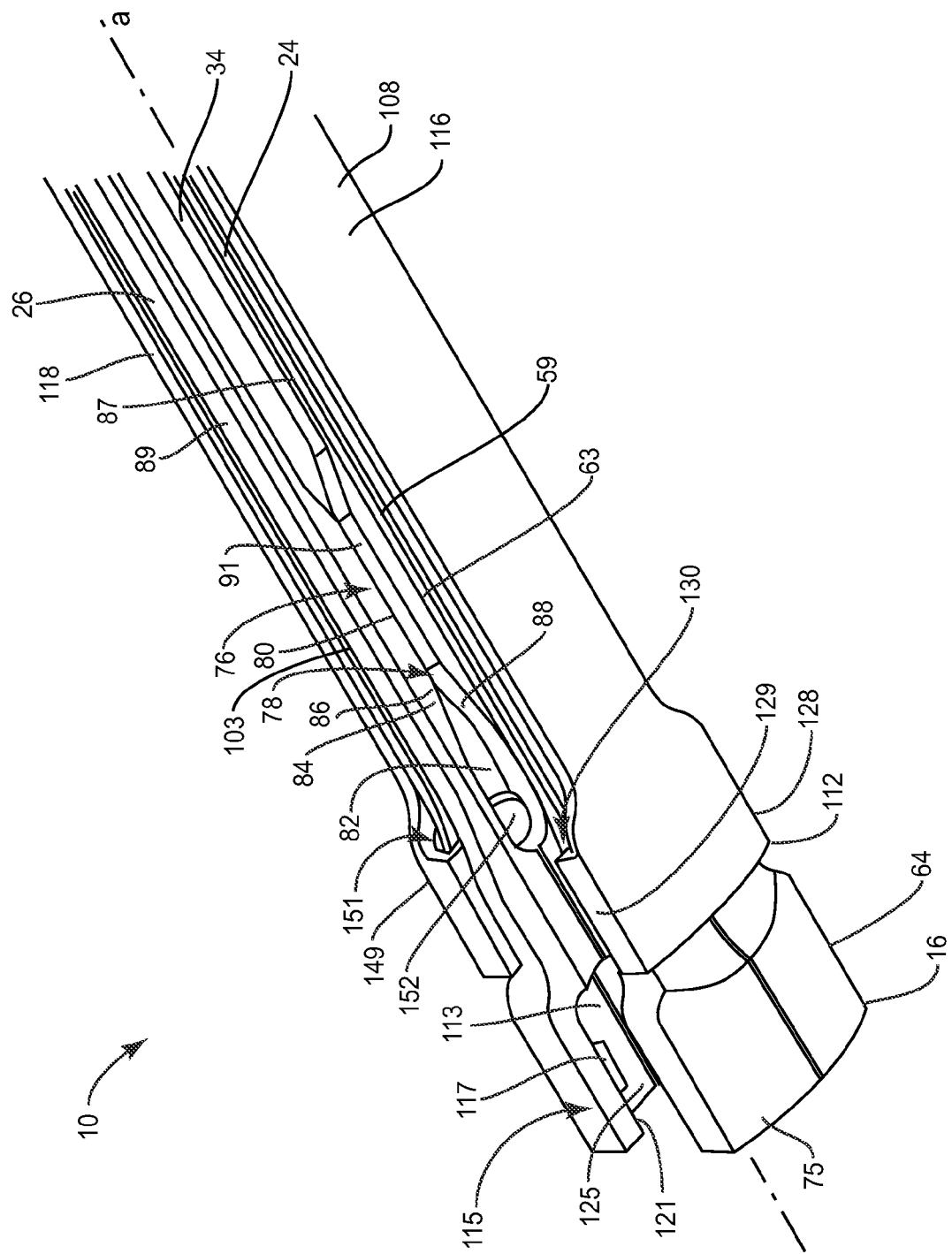
FIG. 3 is an enlarged break away perspective view of the components shown in FIG. 2.

Wall 74 has a first sliding contact surface, which includes a surface 76 and a surface 91, as shown in FIG. 3. Surfaces 76, 91 have a smooth and even configuration for movable engagement with a surface of an outer sleeve, discussed below. It is envisioned that surfaces 76, 91 may have various surface configurations, such as those alternatives described herein.

Surfaces 76, 91 are spaced apart to define an axial cavity, such as, for example, an axial slot 78, similar to slot 38, disposed adjacent distal end 70. Axial slot 78 extends between a proximal portion 80 and a distal portion 82. Surfaces 76, 91 are spaced apart distance d1 adjacent proximal portion 80 in the non-expanded orientation of inner sleeve 12. Inner sleeve 12 is expandable to an expanded orientation such that surfaces 76, 91 are spaced apart distance d2 adjacent proximal portion 80. As such, axial slot 78 can be expanded and contracted adjacent proximal portion 80 within a range of expansion between distance d1 and distance d2.

Surfaces 76, 91 are spaced apart distance d3 adjacent distal portion 82 in the non-expanded orientation of inner sleeve 12. Inner sleeve 12 is expandable to an expanded orientation such that surfaces 76, 91 are spaced apart distance d4 adjacent distal portion 82. As such, axial slot 78 can be expanded and contracted adjacent distal portion 42 within a range of expansion between distance d3 and distance d4.

An intermediate portion 84 of slot 78 is disposed between portions 80, 82. Surface 76 defines a first ramp 86 adjacent intermediate portion 84. Ramp 86 extends between a proximal end and a distal end, which define an inclination therebetween that facilitates expansion of inner sleeve 12 between the non-expanded orientation and the expanded orientation. Surface 91 defines a second ramp 88 adjacent intermediate portion 84. Ramp 88 extends between a proximal end and a distal end, which define an inclination therebetween that facilitates expansion of inner sleeve 12 between the non-expanded orientation and the expanded orientation.

Ramps 86, 88 are spaced apart average distance d5 adjacent intermediate portion 84 in the non-expanded orientation of inner sleeve 12. Inner sleeve 12 is expandable to the expanded orientation such that ramps 86, 88 are spaced apart average distance d6 adjacent intermediate portion 84. As such, axial slot 78 can be expanded and contracted adjacent intermediate portion 84 within a range of expansion between distance d5 and distance d6.

Wall 74 includes flanges 101, 103, similar to flanges 62, 63, located on opposing sides of wall 74. Flange 101 includes a ledge 105 that extends from a proximal end to a distal end. Flange 103 includes a ledge 107 that extends from a proximal end to a distal end. Flanges 101, 103 are configured for engagement with the distal end of an outer sleeve for slidable engagement, as described herein.

Cantilevered arm 87 includes a capture member 104 disposed adjacent distal end 70. Capture member 104 includes an inner surface 109 that defines an implant cavity configured for disposal of at least a portion of an implant, such as, for example, a bone fastener. Inner surface 109 includes at least one fixation surface, such as, for example, a projection 106 that extends into the implant cavity of capture member 104 to engage the bone fastener for retaining the bone fastener with inner sleeve 12. Inner surface 109 includes a planar face 119 and an arcuate face 123. It is contemplated that all or only a portion of inner surface 109 may have alternate surface configurations to enhance fixation with the bone fastener, such as, for example, dimpled and/or textured. It is contemplated that the projection may include a nail configuration, raised elements and/or spikes to facilitate engagement of the capture member with the bone fastener.

Cantilevered arm 89 includes a capture member 115 disposed adjacent a distal end thereof. Capture member 115 includes an inner surface 113 that defines an implant cavity configured for disposal of at least a portion of an implant, such as, for example, a bone fastener. Inner surface 113 includes at least one fixation surface, such as, for example, a projection 117 that extends into the implant cavity of capture member 115 to engage the bone fastener for retaining the bone fastener with inner sleeve 12. Inner surface 113 includes a planar face 121 and an arcuate face 125. It is contemplated that all or only a portion of inner surface 113 may have alternate surface configurations, similar to those described herein.

Capture member 104 extends from arm 87 and capture member 115 extends from arm 89 such that members 104, 115 are biased for engagement due to the bias of arms 87, 89. Members 104, 115 are movable between a non-expanded orientation and an expanded orientation, similar to that discussed above with regard to members 64, 75. In the non-expanded orientation, the surfaces of members 104, 115 are disposed in a flush contacting engagement such that, for example, members 104, 115 capture and/or retain the bone fastener. Projections 106, 117 engage the bone fastener to releasably lock the bone fastener with members 104, 115. Members 104, 115 are expandable and separable, via engagement with the outer sleeve as described herein, to dispose members 104, 115 in the expanded orientation. In the expanded orientation, members 104, 115 are spaced apart such that, for example, members 104, 115 release and/or eject the bone fastener from members 104, 115. Projections 104, 115 disengage from the bone fastener.

A second member, such as, for example, an outer sleeve 108 is configured for slidable engagement with inner sleeve 12. Outer sleeve 108 extends between a proximal end 110 and a distal end 112. Proximal end 110 is mounted with an actuator, as described herein, and relatively fixed thereto.

Outer sleeve 108 extends along longitudinal axis a and is mounted with inner sleeve 12 for axial translation relative to inner sleeve 12. Outer sleeve 108 has a cylindrical cross-section configuration. It is contemplated that the cross-section of outer sleeve 108 may have various configurations, for example, round, oval, rectangular, polygonal, irregular, tapered, offset, staggered, uniform and non-uniform. It is further envisioned that one or all of the surfaces of outer sleeve 108 may have alternate surface configurations, such as, for example, rough, threaded for connection with surgical instruments, arcuate, undulating, porous, semi-porous, dimpled, polished and/or textured according to the requirements of a particular application.

Outer sleeve 108 includes an implant cavity, such as, for example, channel 114 that extends through outer sleeve 108. Channel 114 has a cylindrical cross-section configuration. It is contemplated that the cross-section of channel 114 may have various configurations, for example, round, oval, rectangular, polygonal, irregular, tapered, offset, staggered, uniform and non-uniform. Channel 114 is configured for disposal of inner sleeve 12, as described herein.

Outer sleeve 108 includes two spaced apart second extensions 116, 118. Extension 116 extends between a proximal end 120 and a distal end 122. Intermediate portion 124 is disposed between ends 120, 122. Extension 116 includes flanges 128, 129. Flanges 128, 129 are disposed at distal end 122. Flanges 128, 129 define flange cavities 130 configured for disposal of flanges 62, 63 of inner sleeve 12 such that flanges 128, 129 slidably engage ledges 57, 59 of flanges 62, 63 respectively during, for example, axial translation of the components of system 10.

Extension 116 includes a second sliding contact surface, such as, for example, pin 132. Pin 132 is configured for engagement with surfaces 36, 37 that define axial slot 38. Pin 132 extends in a transverse orientation relative to a longitudinal axis within axial slot 38. Pin 132 engages surfaces 36, 37 such that members 64, 75 are movable between the non-expanded orientation and the expanded orientation, as described herein. It is envisioned that pin 132 can be variously configured with regard to size and shape, and the shape may be rectangular, triangular, polygonal, and hexagonal, for example. It is further envisioned that the sliding contact surface may comprise a hook, clip, rod, tab, detent and/or key/keyway for slidable engagement with inner sleeve 12.

Extension 118 extends between a proximal end 140 and a distal end 142. Intermediate portion 144 is disposed between ends 140, 142. Extension 118 includes flanges 148, 149. Flanges 148, 149 are disposed at distal end 142. Flanges 148, 149 define flange cavities 151 configured for disposal of flanges 101, 103 of inner sleeve 12 such that ledges 95, 97 of flanges 148, 149 slidably engage flanges 101, 103 during, for example, axial translation.

Extension 118 includes a second sliding contact surface, such as, for example, pin 152. Pin 152 is configured for engagement with surfaces 76, 91 that define axial slot 78. Pin 152 extends in a transverse orientation relative to a longitudinal axis within axial slot 78. Pin 152 engages surfaces 76, 91 such that members 104, 115 are movable between the non-expanded orientation and the expanded orientation, as described herein. It is envisioned that pin 152 can be variously configured with regard to size and shape, and the shape may be rectangular, triangular, polygonal, and hexagonal, for example. It is further envisioned that the sliding contact surface may comprise a hook, clip, rod, tab, detent and/or key/keyway for slidable engagement with inner sleeve 12.

An actuator 160 is configured for fixation with outer sleeve 108 and relatively movable engagement with inner sleeve 12, to cause axial translation of inner sleeve 12 relative to outer sleeve 108, as described herein. Actuator 160 extends between a proximal portion 162 and a distal portion 164. An intermediate portion 166 includes an outer surface 168 that is textured with ridges to provide a grip configuration. It is contemplated that outer surface 168 can have alternative surface configurations, similar to those described herein. Actuator 160 has a cylindrical cross-section configuration. It is contemplated that the cross-section of actuator 160 may have various configurations, for example, round, oval, rectangular, polygonal, irregular, tapered, offset, staggered, uniform and non-uniform.

Actuator 160 includes an opening 170 that communicates with an inner surface 172. Inner surface 172 defines a cavity configured for movable disposal of inner sleeve 12 and/or an instrument, such as a driver or reduction device, and/or an implant Inner surface 172 is configured for fixation with outer sleeve 108. Inner surface 172 is threaded for engagement with outer threaded surface 20. Engagement of the threaded surfaces and rotation of actuator 160 causes axial translation of inner sleeve 12 relative to outer sleeve 108, as described herein.

Spinal implant system 10 includes a bone fastener 180. Bone fastener 180 includes a proximal portion, such as for example, a receiver 182 and a distal portion, such as for example, a shaft 194, as shown in FIG. 1. Receiver 182 includes a pair of spaced apart walls 181, 183 defining an implant cavity 184. It is envisioned that walls 181, 183 may have uniformly increasing or decreasing taper, arcuate, staggered and/or offset portions. In one embodiment, the inner surfaces of walls 181, 183 may include internal threads. Internal threads may be configured to receive a set screw to fix the position of a vertebral rod, for example, within implant cavity 184 of bone fastener 180. It is envisioned that internal threads may be reverse angle threads such that threads may include a forward face that points down and in toward implant cavity. In one embodiment, implant cavity 184 is generally U-shaped and is configured to receive a cylindrical spinal construct, such as, for example, a vertebral rod. It is contemplated that the cross-section of the vertebral rod may have various configurations, for example, round, oval, rectangular, polygonal, irregular, tapered, offset, staggered, uniform and non-uniform. It is envisioned that implant cavity 184 may have other configurations, including, for example, V-shaped, polygonal, or tapered depending upon the geometry of the spinal construct to be received within implant cavity 184.

Walls 181, 183 include a first outer surface 187 defining a first locking cavity, such as, for example an elongated locking slot 188 and a second outer surface 191 defining a second locking cavity, such as, for example an elongated locking slot 192. Locking slots 188 are configured to receive projections 66, 77 and locking slots 192 are configured to receive projections 106, 117, for releasably locking bone fastener 180 with inner sleeve 12. It is envisioned that locking slots 188 and 192 may have other cross-sectional configurations, including, for example, flat bottomed channel, a cut similar to a rack and pinion, V-shaped, W-shaped, polygonal or tapered. It is further envisioned that one or both of slots 188 and 192 may be transversely oriented relative to a longitudinal axis of bone fastener 180, such as, for example, perpendicular, angled, and/or may be disposed in parallel orientation. It is contemplated that slots 188 and 192 allow bone fastener 180 to be captured and retained under tension and lateral compression by inner sleeve 180. It is envisioned that one or all of the surfaces of walls 181, 183 have alternate surface configurations, such as, for example, rough, threaded for connection with surgical instruments, arcuate, undulating, porous, semiporous, dimpled, polished and/or textured according to the requirements of a particular application.

It is contemplated that shaft 194 or portions thereof can have various dimensions, for example, with regard to length, width, diameter, and thickness. Shaft 194 is threaded along the length thereof and configured for penetrating tissue. Shaft 194 has a cylindrical cross section configuration and includes an outer surface having an external thread form. It is contemplated that the thread form may include a single thread turn or a plurality of discrete threads. It is further contemplated that other engaging structures may be located on shaft 194, such as, for example, a nail configuration, barbs, expanding elements, raised elements and/or spikes to facilitate engagement of shaft 194 with tissue, such as, for example, vertebrae.

It is envisioned that all or only a portion of shaft 194 may have alternate cross section configurations, such as, for example, oval, oblong, triangular, square, polygonal, irregular, uniform, non-uniform, offset, staggered, undulating, arcuate, variable and/or tapered. It is contemplated that the outer surface of shaft 194 may include one or a plurality of openings. It is further contemplated that all or only a portion of the outer surface of shaft 194 may have alternate surface configurations to enhance fixation with tissue such as, for example, rough, arcuate, undulating, mesh, porous, semiporous, dimpled, and/or textured according to the requirements of a particular application. It is envisioned that all or only a portion of shaft 194 may be disposed at various orientations, relative to the longitudinal axis of bone fastener 180, such as, for example, transverse, perpendicular and/or other angular orientations such as acute or obtuse and/or may be offset or staggered. It is further envisioned that all or only a portion of shaft 194 may be cannulated.

In operation, members 64, 75 of extension 24 and members 104, 115 of extension 26 are disposed in the non-expanded orientation and bone fastener 180 is disposed adjacent distal end 16, as shown in FIG. 1. Pin 132 is disposed with distal portion 42 of slot 38, as shown in FIG. 8, and pin 152 is disposed with distal portion 82 of slot 78, as shown in FIG. 3.

Figure 5:
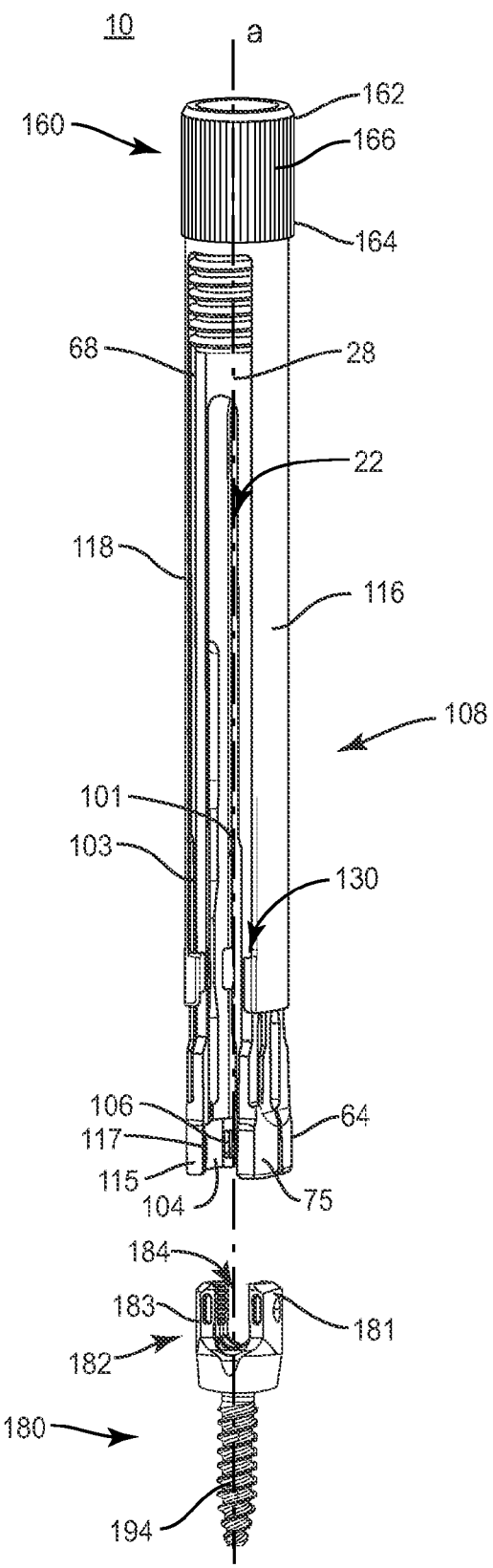
FIG. 5 is a front view of the system shown in FIG. 1.

To attach bone fastener 180 with inner sleeve 12, a medical practitioner rotates actuator 160 in a direction, such as, for example, a counter clockwise direction to axially translate inner sleeve 12, in a first direction as shown by arrow A in FIG. 1, relative to outer sleeve 108. Actuator 160 is rotated and pins 132, 152 axially translate within slots 38, 78 to intermediate portions 44, 84 such that pins 132, 152 engage ramps 46, 48 and 86, 88, as shown in FIG. 7 for example. Pins 132, 152 engage ramps 46, 48 and 86, 88 to drive and space apart arms 31, 32. Pins 132, 152 axially translate along slots 38, 78 to proximal portions 40, 80 such that arms 31, 32 are spaced apart distance d2 adjacent proximal portions 40, 80. Members 64, 75, 104, 115 expand and separate to dispose members 64, 75, 104, 115 in the expanded orientation, as shown in FIGS. 4 and 5.

Figure 6:
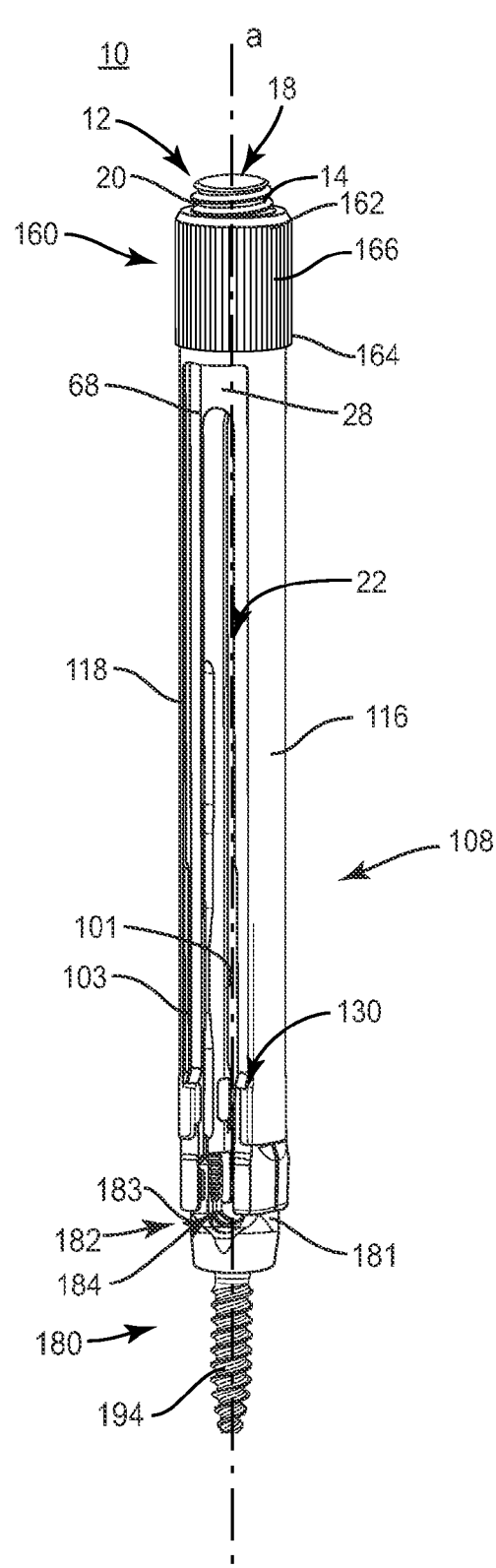
FIG. 6 is a front view of the system shown in FIG. 1.

In the expanded orientation, distal end 16 extends from distal end 112 to engage bone fastener 180. Projections 66, 77 and 106, 117 are manipulated to engage slots 188, 192, to capture bone fastener 180, as shown in FIG. 6. To provisionally capture bone fastener 180, the medical practitioner rotates actuator 160 in a direction, such as, for example, a clockwise direction to axially translate inner sleeve 12, in a second direction as shown by arrow B in FIG. 1, relative to outer sleeve 108. Actuator 160 is rotated and pins 132, 152 axially translate within slots 38, 78 from proximal portions 40, 80 to intermediate portions 44, 84 such that pins 132, 152 exit proximal portions 40, 80. Arms 31, 32 contract and pins 132, 152 are disposed between ramps 46, 48 and 86, 88, as shown in FIG. 7. Members 64, 75, 104, 115 contract to provisionally capture bone fastener 180 in a non-expanded orientation, as shown in FIG. 7. Actuator 160 is rotated and pins 132, 152 axially translate within slots 38, 78 to distal portions 42, 82 such that bone fastener 180 is disposed with inner sleeve 12 in a locked position, as shown in FIG. 8.

To eject and/or release bone fastener 180 from inner sleeve 12, the medical practitioner rotates actuator 160 in the counter clockwise direction to axially translate inner sleeve 12 in the direction shown by arrow A, relative to outer sleeve 108. Actuator 160 is rotated and pins 132, 152 axially translate within slots 38, 78 to intermediate portions 44, 84 such that pins 132, 152 engage ramps 46, 48 and 86, 88 to drive and space apart arms 31, 32. Pins 132, 152 axially translate along slots 38, 78 to proximal portions 40, 80 such that arms 31, 32 are spaced apart distance d2 adjacent proximal portions 40, 80. Members 64, 75, 104, 115 expand and separate to dispose members 64, 75, 104, 115 in the expanded orientation, as shown in FIG. 4. In the expanded orientation, distal end 16 extends from distal end 112 to release bone fastener 180. Projections 66, 77 and 106, 117 are manipulated to disengage from slots 188, 192, to eject bone fastener 180.

Figure 9:
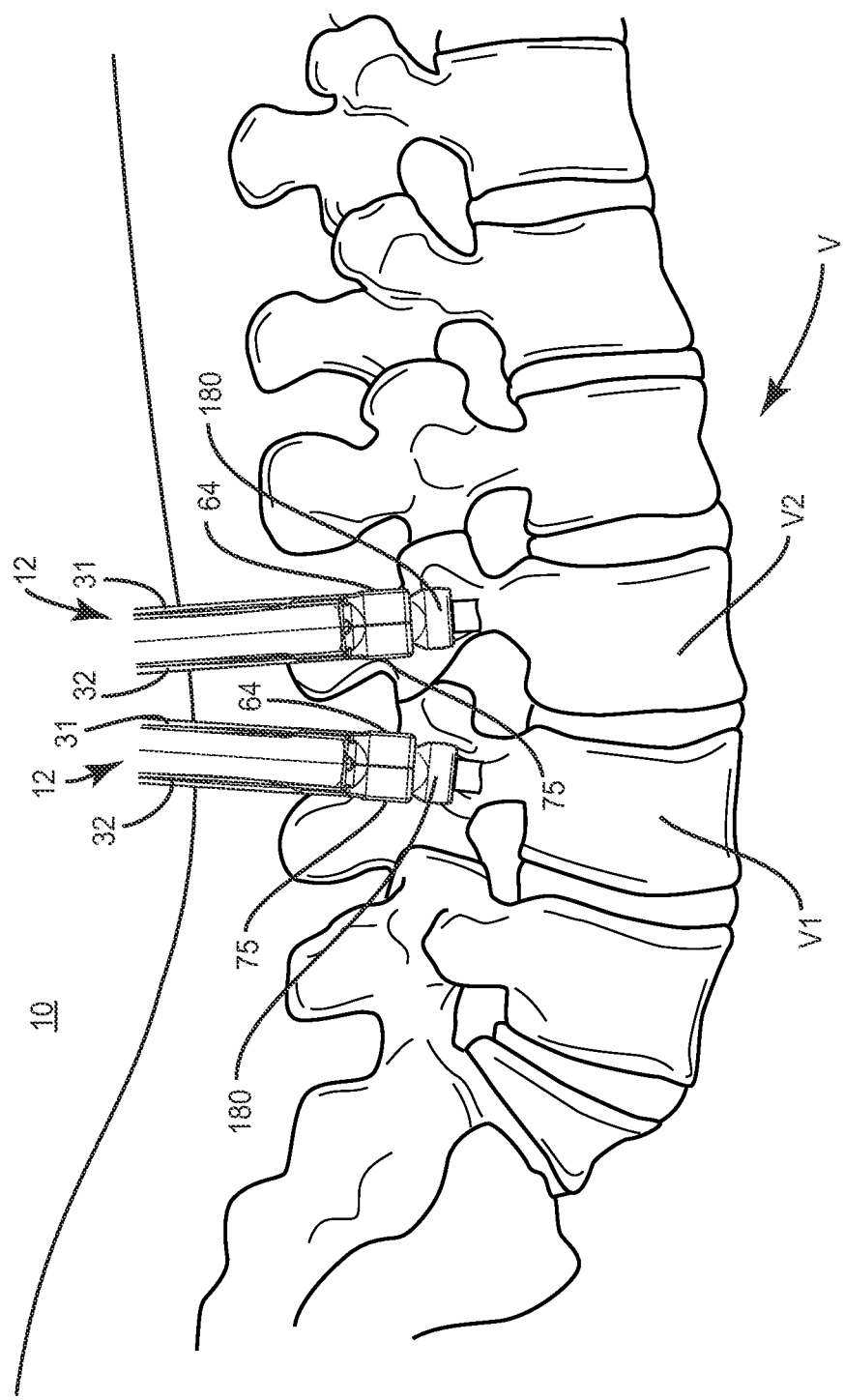
FIG. 9 is a side view of one embodiment of a system in accordance with the principles of the present disclosure disposed with vertebrae.

In assembly, operation and use, the spinal implant system 10, similar to that described herein, is employed with a surgical procedure for treatment of a spinal disorder affecting a section of a spine of a patient, as discussed herein. Spinal implant system 10 may also be employed with other surgical procedures. For example, spinal implant system 10 can be used with a surgical procedure for treatment of a condition or injury of an affected section of the spine including vertebrae V, as shown in FIG. 9.

In use, to treat the affected section of vertebrae V, a medical practitioner obtains access to a surgical site including vertebrae V1, V2 in any appropriate manner, such as through incision and retraction of tissues. It is envisioned that the spinal implant system 10 may be used in any existing surgical method or technique including open surgery, mini-open surgery, minimally invasive surgery, and percutaneous surgical implantation, whereby vertebrae is accessed through a micro-incision, or sleeve that provides a protected passageway to the area. Once access to the surgical site is obtained, the particular surgical procedure is performed for treating the spinal disorder. The spinal implant system is then employed to augment the surgical treatment. The spinal implant system can be delivered or implanted as a pre-assembled device or can be assembled in situ. The spinal implant system 10 may be completely or partially revised, removed or replaced, for example, removing bone fastener 180, inner sleeve 12 and/or outer sleeve 108, a vertebral rod and/or one or all of the components of the spinal implant system during or after the surgical procedure.

Pilot holes or the like are made in vertebrae V1, V2 for receiving shaft 194 of bone fastener 180. The spinal implant system 10 is disposed adjacent vertebrae V at a surgical site and the components of spinal implant system 10 are manipulable to drive, torque, insert or otherwise connect bone fastener 180 to vertebrae and/or dispose a vertebral construct, such as, for example, a vertebral rod (not shown) with bone fastener 180, according to the particular requirements of the surgical treatment.

Extensions 24, 26 are disposed in the non-expanded orientation, as described above, and bone fastener 180 is disposed adjacent distal end 16. The medical practitioner rotates actuator 160 in a counter clockwise direction to axially translate inner sleeve 12 (shown by arrow A in FIG. 1) relative to outer sleeve 108. Actuator 160 is rotated and pins 132, 152 axially translate to engage ramps 46, 48 and 86, 88 to drive and space apart arms 31, 32 for disposal with proximal portions 40, 80 such that arms 31, 32 are spaced apart.

Distal end 16 extends from distal end 112 and members 64, 75, 104, 115 expand and separate to engage bone fastener 180. Projections 66, 77 and 106, 117 are manipulated to engage slots 188, 192, to capture bone fastener 180, as shown in FIG. 6. Actuator 160 is rotated in a clockwise direction to axially translate inner sleeve 12 (shown by arrow B in FIG. 1) relative to outer sleeve 108 to provisionally capture bone fastener 180 such that members 64, 75, 104, 115 contract to provisionally capture bone fastener 180 in a non-expanded orientation. Actuator 160 is further rotated such that bone fastener 180 is disposed with inner sleeve 12 in a locked position, as described. In one embodiment, inner sleeve 12, fixed with bone fastener 180, may apply torque and/or rotation to bone fastener 180 for driving shaft 194 into vertebrae V.

To eject bone fastener 180 from inner sleeve 12, the medical practitioner rotates actuator 160 in the counter clockwise direction such that members 64, 75, 104, 115 are expanded and separated to dispose members 64, 75, 104, 115 in the expanded orientation. In the expanded orientation, distal end 16 extends from distal end 112 to release bone fastener 180. Projections 66, 77 and 106, 117 are manipulated to disengage from slots 188, 192, to eject bone fastener 180. Upon completion of the procedure, the surgical instruments and assemblies are removed from the surgical site and the incision is closed.

Bone fastener 180 may be employed as a bone screw, pedicle screw, or multi-axial screw used in spinal surgery. It is contemplated that bone fastener 180 may be coated with an osteoconductive material such as hydroxyapatite and/or osteoinductive agent such as a bone morphogenic protein for enhanced bony fixation. Bone fastener 180 can be made of radiolucent materials such as polymers. Radiomarkers may be included for identification under x-ray, fluoroscopy, CT, or other imaging techniques. Metallic or ceramic radiomarkers, such as tantalum beads, tantalum pins, titanium pins, titanium endcaps, and platinum wires can be used.

Figure 10:
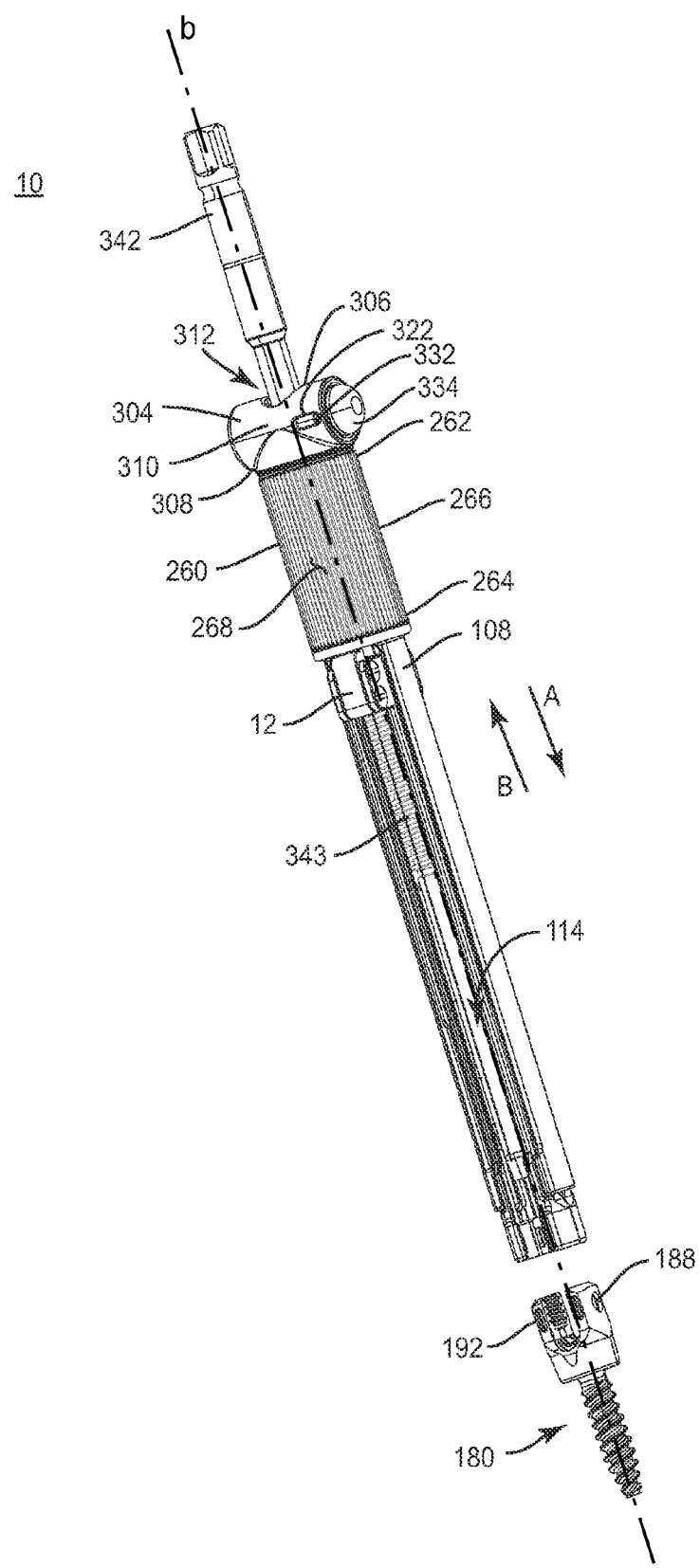
FIG. 10 is a perspective view of one embodiment of a system in accordance with the principles of the present disclosure.
Figure 11:
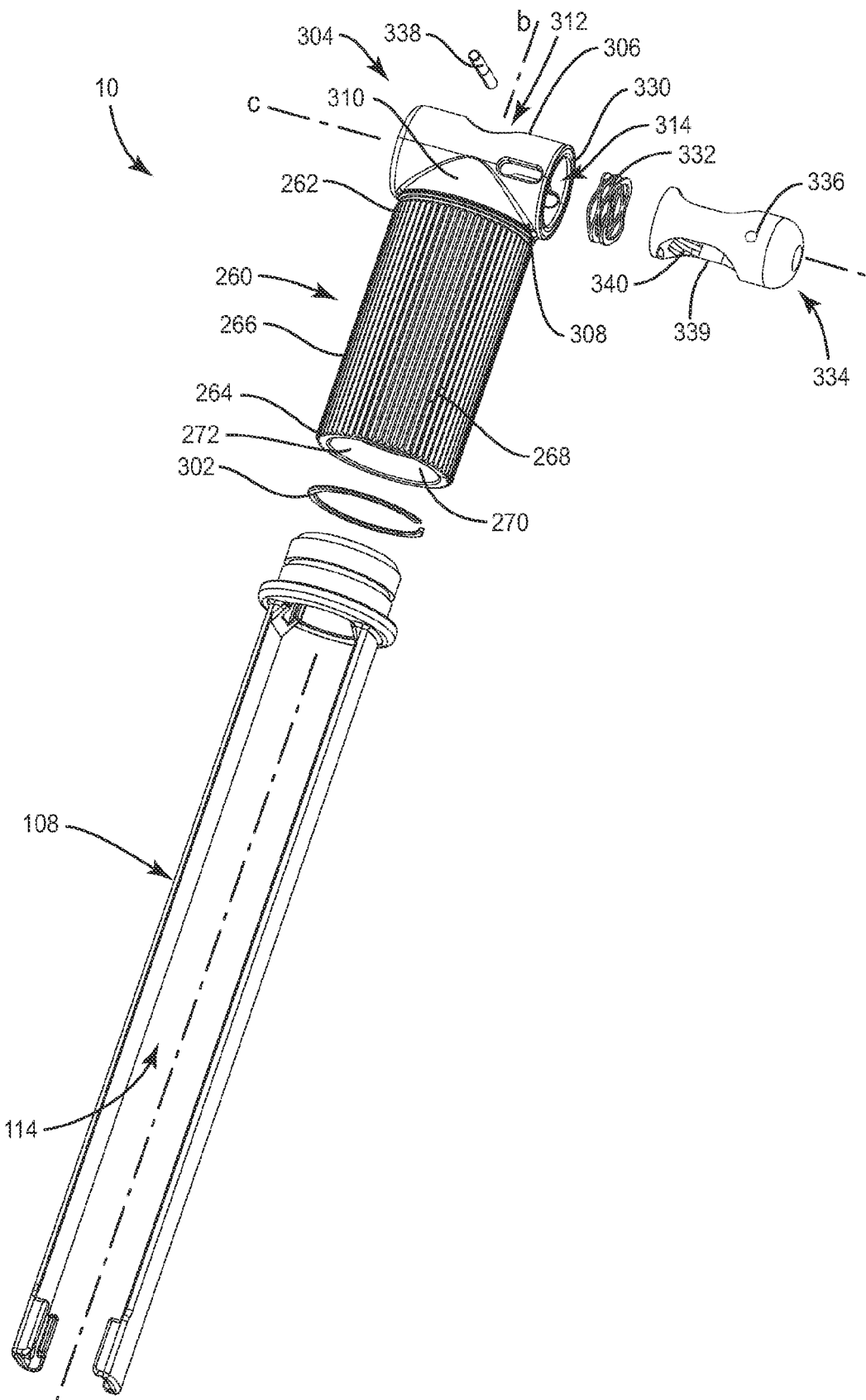
FIG. 11 is a perspective view of components of the system shown in FIG. 10 with parts separated.

In one embodiment, as shown in FIGS. 10-11, spinal implant system 10, similar to the apparatus and methods described above with regard to FIGS. 1-9, includes inner sleeve 12 and outer sleeve 108 described above. An actuator 260, similar to actuator 160 described above, is configured for fixation with outer sleeve 108 and relatively movable engagement with inner sleeve 12, to cause axial translation of inner sleeve 12 relative to outer sleeve 108, as described. Actuator 260 extends between a proximal portion 262 and a distal portion 264. Actuator 260 includes a snap ring 302 disposed at distal portion 264. Snap ring 302 is configured to facilitate retention of outer sleeve 108 with actuator 260.

Intermediate portion 266 of actuator 260 extends between portions 262, 264. Intermediate portion 266 includes an outer surface 268 that is textured with ridges to provide a grip configuration. It is contemplated that outer surface 268 can have alternative surface texture configurations, similar those described herein. Actuator 260 has a cylindrical cross-section configuration. It is contemplated that the cross-section of actuator 260 may have various configurations, similar those described herein. Actuator 260 includes an opening 270 configured to receive snap ring 302 and outer sleeve 108 for mounting actuator 260 with outer sleeve 108. Actuator 260 includes an inner surface, similar to inner surface 172 that is threaded for engagement with outer threaded surface 20. Engagement of the threaded surfaces and rotation of actuator 260 causes axial translation of inner sleeve 12 relative to outer sleeve 108, as described herein.

Proximal end 262 includes a button housing 304 that includes a coupling element for engaging and disengaging an instrument 342 disposed with actuator 260. Housing 304 is engageable with instrument 342 in a first orientation to facilitate a precise or fine control of axial translation of instrument 342 for engagement with an implant, such as, for example, bone fastener 180 described above. Housing 304 can be disengaged from instrument 342 in a second orientation to facilitate a quick slidable translation and/or movement of instrument 342 to a site adjacent bone fastener 180. This configuration expedites delivery of instrument 342 to the site during a procedure.

Button housing 304 extends between a proximal end 306 and a distal end 308. Intermediate portion 310 extends between ends 306, 308. Proximal end 306 includes opening 312 that defines a longitudinal axis b. It is contemplated that the shape of opening 312 may have various configurations, for example, oval, rectangular, polygonal, irregular, tapered, offset, staggered, uniform and non-uniform. Opening 312 communicates with channel 314 that extends through housing 304. Channel 314 defines a transverse axis c. Intermediate portion 310 includes a slot 322 configured for engagement with a pin, as described herein.

Button housing 304 includes an opening 330 that communicates with channel 314. Opening 330 is configured for disposal of a coupling element, such as, for example, a button, as described herein. Button housing 304 includes a biasing member, such as, for example, a spring 332 disposed within channel 314 and being configured to engage a button 334. Button 334 is disposed for relative movement within channel 314 and retained therein via a pin 338. Pin 338 is disposed within a cavity 336 of button 334. Movement of button 334 is limited by engagement of pin 338 with the surfaces of slot 322.

Button 334 is a depressible member and includes an inner threaded surface 339 that defines an opening 340 that is aligned with longitudinal axis b upon disposal of button 334 with button housing 304. Openings 312, 340 are configured for disposal and movable passage therethrough of instrument 342, such as, for example, torque devices, screw drivers, extenders, inserters, reducers, rod delivery adaptors, bone fasteners and/or vertebral constructs, which may be alternately sized and dimensioned. Surface 339 is threaded and configured as a movable coupling element for engagement with a threaded surface 343 of instrument 342. Surface 339 is movable relative to button housing 304.

In operation, upon fixation of bone fastener 180 with vertebrae V, as described above with regard to FIGS. 1-9, instrument 342 is placed within openings 312, 340 for passage through channel 114 to adjacent bone fastener 180 and/or an adjacent surgical site in connection with a treatment or procedure.

Spring 332 biases button 334 to the first orientation such that threaded surface 339 threadably engages threaded surface 343. In the first orientation, instrument 342 is rotatable in a direction, such as, for example, a clockwise direction such that instrument 342 is axially translatable, in the direction shown by arrow A in FIG. 10, relative to button housing 304 and in a direction, such as, for example, a counter clockwise direction such that instrument 342 is axially translatable, in the direction shown by arrow B in FIG. 10, relative to button housing 304. In the first orientation, free slidable axial translation of instrument 342 relative to button housing 304 is prevented due to the engagement of surfaces 339, 343.

Button 334 is depressible to overcome the bias of spring 332 to drive button 334 into button housing 304. This actuation disengages threaded surface 339 from threaded surface 343 such that instrument 342 is released from housing 304 to a second orientation. Disengagement of instrument 342 from housing 304 allows free slidable axial translation of instrument 342 relative to button housing 304 in the directions shown by arrow A and arrow B. This configuration of system 10 in the second orientation provides a quick slidable translation and/or movement of instrument 342 to a site adjacent bone fastener 180. A distal end of instrument 342 is freely slid to a site adjacent bone fastener 180 and/or the surgical site for engagement, for example, with a set screw to fix and/or lock a spinal rod with bone fastener 180.

Button 334 is released such that spring 332 biases button 334 to the first orientation such that threaded surface 339 threadably engages threaded surface 343. Instrument 342 is rotatable, as described above, to cause axial translation of the distal end of instrument 342 to facilitate a precise or fine control of axial translation of instrument 342 for engagement and applying torque to the set screw. Other instruments, such as those described herein, may be similarly engaged with button housing 304 and passed through channel 114 to adjacent bone fastener 180 and/or an adjacent surgical site in connection with a treatment or procedure.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An extender comprising:
   a first extension including a first wall and extending between a proximal end and a distal end, the first wall defining an axial cavity including a distal portion having a first dimension, an intermediate portion having at least one ramp and a proximal portion having a second dimension, the first dimension being greater than the second dimension, the distal end including at least one fixation surface;
   a second extension extending from adjacent the proximal end of the first extension to a distal end of the second extension, the distal end including a projection; and
   an actuator fixed with the second extension, the proximal end of the first extension including a threaded outer surface, the actuator including an inner surface having a first threaded surface engageable with the threaded outer surface to cause axial translation,
   wherein the first extension is configured for axial translation relative to the second extension such that the projection is disposable in the axial cavity in a first position such that the projection is disposed with the distal portion of the axial cavity and the distal end of the first extension is disposed in a non-expanded orientation, and the projection is slidably engageable with the at least one ramp for movement to a second position such that the projection is disposed with the proximal portion of the axial cavity and the distal end of the first extension is disposed in an expanded orientation.

2. An extender as recited in claim 1, wherein the first extension includes two spaced apart first extensions.

3. An extender as recited in claim 1, wherein the first wall includes a first ramp and a second ramp disposed adjacent the intermediate portion, the ramps being spaced apart to define the second dimension.

4. An extender as recited in claim 1, wherein the at least one ramp includes a first flange and the distal end of the second extension includes a second flange that defines a flange cavity configured for disposal of the first flange such that the second flange slidably engages the first flange during axial translation.

5. An extender as recited in claim 1, wherein the distal end of the first extension includes an inner surface that includes the at least one fixation surface, the at least one fixation surface including a first projection and a second projection.

6. An extender as recited in claim 1, wherein the inner surface of the actuator defines a cavity configured for movable disposal of an instrument.

7. An extender as recited in claim 6, wherein the inner surface of the actuator includes a second threaded surface engageable with the instrument to cause axial translation of the instrument relative to the first extension.

8. An extender as recited in claim 7, wherein the actuator includes a coupling element that disengages the instrument from the second threaded surface to facilitate slidable axial translation of the instrument relative to the first extension.

9. An extender as recited in claim 1, wherein the first extension includes two spaced apart first extensions that each comprise spaced apart cantilevered arms.

10. An extender as recited in claim 9, wherein the cantilevered arms of each of the first extensions are biased inwardly toward each other.

11. An extender as recited in claim 9, wherein the at least one fixation surface comprises a projection extending from each of the cantilevered arms.

12. An extender as recited in claim 1, wherein the projection is a pin that extends in a transverse orientation relative to a longitudinal axis within the axial cavity.

13. An extender comprising:
a first member defining a first longitudinal axis and extending between a proximal end and a distal end, the first member including two spaced apart first extensions, each of the first extensions including a wall including a first sliding contact surface that defines an axial slot including a distal portion having a first dimension, an intermediate portion having at least one ramp and a proximal portion having a second dimension, the first dimension being greater than the second dimension, each of the first extensions including an expandable capture member having at least one fixation surface adjacent the distal end; and
a second member extending from adjacent the proximal end of the first member to a distal end of the second member, the second member including two spaced apart second extensions, each of the second extensions including a projection having a second sliding contact surface; and
an actuator fixed with the second member, the proximal end of the first member including a threaded outer surface, the actuator including an inner surface having a first threaded surface engageable with the threaded outer surface to cause the axial translation,
wherein the first member is configured for axial translation in a first direction relative to the second member such that the projections are disposable in respective axial slots in a first position such that each of the projections are disposed with the distal portion of the respective axial slot and the respective capture member is disposed in a non-expanded orientation, and the first sliding contact surfaces are engageable with the second sliding contact surfaces for movement to a second position such that the projections are disposed with the proximal portion of the axial slot and a respective capture member is disposed in an expanded orientation.

14. An extender as recited in claim 13, wherein the at least one ramp is tapered in a distal to a proximal orientation.

15. An extender as recited in claim 13, wherein the first sliding contact surface of each of the first extensions includes a first ramp and a second ramp respectively disposed adjacent the intermediate portion, the ramps being spaced apart to define the second dimension.

16. An extender as recited in claim 13, wherein the wall of at least one of the first extensions includes a first flange and the distal end of at least one of the second extensions includes a second flange that defines a flange cavity configured for disposal of the first flange such that the second flange slidably engages the first flange during axial translation.

17. An extender as recited in claim 13, wherein the at least one fixation surface includes a first projection and a second projection.

18. An extender as recited in claim 13, wherein the inner surface of the actuator defines a cavity configured for movable disposal of an instrument.

19. An extender as recited in claim 18, wherein the inner surface of the actuator includes a second threaded surface engageable with the instrument to cause axial translation of the instrument relative to the first member.

20. A spinal implant system comprising:
an extender comprising a first member defining a first longitudinal axis and extending between a proximal end and a distal end, the first member including a pair of spaced apart first extensions, each of the first extensions including a wall including a first sliding contact surface that defines an axial slot including a distal portion having a first dimension, an intermediate portion having a first ramp and a second ramp and a proximal portion having a second dimension, the first dimension being greater than the second dimension, the ramps being tapered to the second dimension, the wall of each of the first extensions including a first flange, each of the first extensions including an expandable capture member having at least one fixation surface adjacent the distal end,
a second member extending from adjacent to the proximal end of the first member to a distal end of the second member, the second member including a pair of spaced apart second extensions, each of the second extensions including a projection including a second sliding contact surface, the distal end of each of the second extensions including a second flange that defines a flange cavity configured for disposal of the first flange such that the second flange slidably engages the first flange, and
an actuator fixed with the second member, the proximal end of the first member including a threaded outer surface, the actuator including a threaded inner surface engageable with the threaded outer surface to cause axial translation of the first member relative to the second member; and
a bone fastener including a proximal portion that defines an implant cavity and a distal portion configured to penetrate tissue,
wherein the actuator is engageable to cause the axial translation of the first member in a first direction relative to the second member such that the projections are disposable in respective axial slots in a first position such that each of the projections are disposed with the distal portion of a respective axial slot and the respective capture member is disposed in a non-expanded orientation such that the at least one fixation surface captures the bone fastener, and the first sliding contact surfaces are engageable with the second sliding contact surfaces for movement to a second position such that the projections are disposed with the proximal portion of the axial slot and the respective capture member is disposed in an expanded orientation to release the bone fastener.

* * * * *